US00PP08871P

United States Patent [19]

Kordes

[11] Patent Number: Plant 8,871

[45] Date of Patent: Aug. 30, 1994

[54] SHRUB ROSE PLANT NAMED KORISSEL

[75] Inventor: Wilhelm Kordes, Sparrieshoop, Fed. Rep. of Germany

[73] Assignee: Bear Creek Gardens, Inc., Medford, Oreg.

[21] Appl. No.: 126,387

[22] Filed: Sep. 22, 1993

[51] Int. Cl.[5] ..... A01H 5/00

[52] U.S. Cl. ..... Plt./1

[58] Field of Search ..... Plt. 1, 23

*Primary Examiner*—Howard J. Locker

*Attorney, Agent, or Firm*—Klarquist Sparkman Campbell Leigh & Whinston

[57] ABSTRACT

Rose plant of the shrub class having small, white, five pelalled flowers borne in large clusters; small, dark green foliage that is resistant to rust and powdery mildew; and a low growing and spreading plant habit.

1 Drawing Sheet

The present invention relates to a new and distinct variety of rose plant of the shrub class which was originated by me by crossing the variety Yesterday, with the variety Edelweiss.

The primary objective of this breeding was to produce a new rose variety having the small, glossy, dark green foliage, low growing habit and vigor of the female parent combined with the large clusters and plant health of the male parent. The objective was substantially achieved, along with other desirable improvements, as evidenced by the following unique combination of characteristics that are outstanding in the new variety and that distinguish if from its parents, as well as from all other varieties of which I am aware:

1. Low growing and spreading plant habit;
2. Small, glossy, dark green foliage;
3. Resistant to several rose plant diseases; and
4. Small, simple white flowers borne in large clusters.

Asexual reproduction of this new variety by softwood cuttings, as performed at Wasco, Calif., and Sparrieshoop, Germany, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Yesterday.

*Pollen parent.*—Edelweiss.

Classification:

*Botanical.*—*Rosa hybrida.*

Commercial.—Shrub.

FLOWER

Observations made from specimens grown in garden environments in Somis, Calif., and Sparrieshoop, Germany, from March to July, 1993.

Blooming habit: Continuous.

Bud:

*Size.*—½ inch in length when the petals start to unfurl.

*Form.*—Short, pointed ovoid.

*Color.*—When sepals first divide, bud color is Red Group 49D at the petal tips; White Group 155D on the rest of the petals. When half blown, the upper and lower sides of the petals are White Group 155D.

*Sepals.*—Color: Green Group 138B. Surface texture: Covered in fine hairs. There are three lightly appendaged sepals. There are two unappendaged sepals with hairy edges.

*Receptacle.*—Color: Green Group 137C. Shape: Pear. Size: Small (3/16 inch×2/16 inch). Surface: Glandular.

*Peduncle.*—Length: Short (¾inch). Surface: Glandular. Color: Medium green and bronzy in areas exposed to the sun. Strength: Stiff, erect and slender.

Bloom:

*Size.*—Small. Average open size is 1½ to 1¾ inches in diameter.

*Borne.*—Several together in pyramidal clusters of 5 to 30 flowers.

*Stems.*—Short (6 inches) and strong.

*Form*—When first open: High centered. permanence: Flattens.

*Petalage.* —Number of petals under normal conditions: 5.

*Color.*—The upper and reverse sides of the petals are White Group 155D. The major color on the upper side is White Group 155D.

*Variegations.*—None.

*Discoloration.*—The general tonality at the end of the first and third days: No change.

*Fragrance.*—Slight.

Petals:

*Texture.*—Thin.

*Shape.*—Oval.

*Form.*—Flat.

*Arrangement.*—Imbricated, with no petaloids in the center.

*Persistence.*—Drop off cleanly.

*Lastingness.*—On the plant: Short (4 days). As a cut flower: Short (3 days).

Reproductive parts:

*Anthers.*—Size: Small. Quantity: Many. Color: Yellow. Arrangement: Regular around the styles.
*Filaments.*—Color: Greenish white.
*Pollen.*—Color: Gold-yellow.
*Styles.*—Color: Greenish white.
*Stigmas.*—Color: Greenish white.

Form: Bush.

Growth: Very vigorous, branching, sprawling. Height at 2 years in California is 2 feet and width is about 4 feet.

Foliage:
Number of leaflets on normal mid-stem leaves.—5 or 7.
*Size.*—Small (4 inches×2½ inches).
*Quantity.*—Abundant.
*Color.*—New foliage: Green Group 137C. Old foliage: Green Group 137A.

Leaflets:
*Shape.*—Pointed oval.
*Texture.*—Upper side: Leathery and glossy.
*Edge.*—Serrated
*Serration.*—Single and small.
*Petiole rachis.*—Color: Reddish when young, becoming green.
*Petiole underside.*—Smooth with occasional prickles and glands.

*Stipules.*—Long (½ inch) and bearded.
*Disease resistance.*—Resistant to mildew and rust under normal growing conditions at Somis, Calif., and Sparrieshoop, Germany.

Wood:
*New wood.*—Color: Reddish. Bark: Smooth.
Old wood.—Color: Green. Bark: Smooth.

Prickles:
*Quantity*—Many on main canes from base. Many on laterals from main canes.
*Form.*—Medium to short (174 inch) and hooked downward.
*Color when young.*-Red.

Small prickles:
*Quantity.*—Few on main stalks. Many on laterals.
*Color.*—Brown.

I claim:

1. A new and distinct variety of rose plant of the shrub class, substantially as herein shown and described, characterized particularly as to novelty by its small, white, five-petalled flowers that are borne in large clusters; its resistance to powdery mildew and rust; its small, dark green, glossy foliage and its low growing and spreading plant habit.

* * * * *

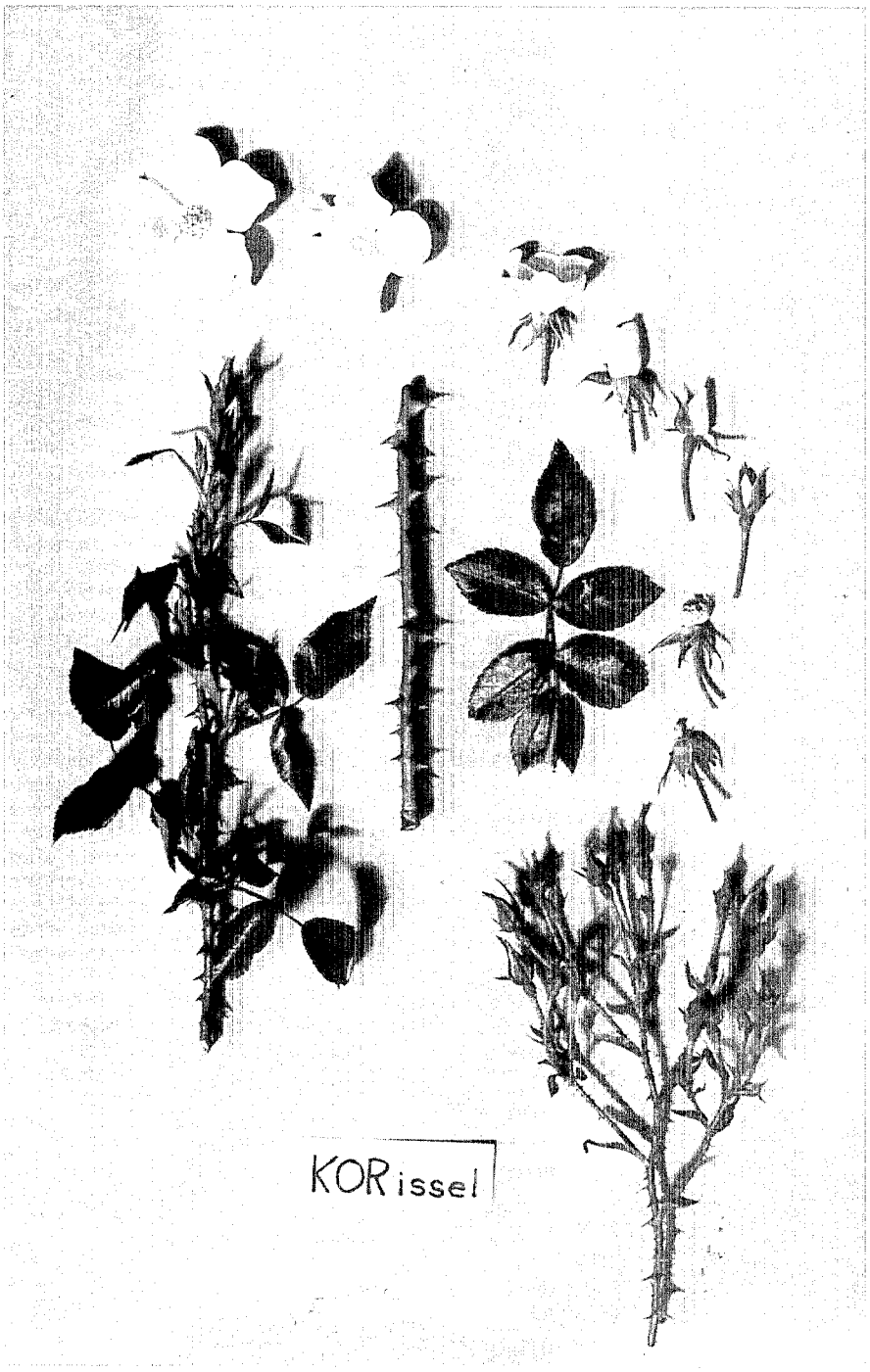
KORissel

UNITED STATES PATENT AND TRADEMARK OFFICE

CERTIFICATE OF CORRECTION

PATENT NO. : PP 8,871

DATED : August 30, 1994

INVENTOR(S) : Wilhelm Kordes

It is certified that error appears in the above-identified patent and that said Letters Patent is hereby corrected as shown below:

Title page, item [57], col. 2,

In the Abstract:

Column 2, Line 2, "pelalled" should read --petaled--.

Column 4, Line 11, "174 inch" should read --1-1/4 inch--.

Signed and Sealed this

Third Day of January, 1995

Bruce Lehman

BRUCE LEHMAN

*Commissioner of Patents and Trademarks*

*Attest:*

*Attesting Officer*